US012570601B2

(12) United States Patent
Bellandi et al.

(10) Patent No.: US 12,570,601 B2
(45) Date of Patent: Mar. 10, 2026

(54) PROCESS FOR PREPARING (R)-4-AMINOINDANE AND CORRESPONDING AMIDES

(71) Applicant: FMC AGRO SINGAPORE PTE. LTD., Singapore (SG)

(72) Inventors: Paolo Bellandi, Carcare (IT); Giampaolo Zanardi, Novara (IT); Pierangelo Mereghetti, Inveruno (IT)

(73) Assignee: FMC AGRO SINGAPORE PTE. LTD., Singapore (SG)

( * ) Notice: Subject to any disclaimer, the term of this patent is extended or adjusted under 35 U.S.C. 154(b) by 419 days.

(21) Appl. No.: 17/639,395

(22) PCT Filed: Sep. 23, 2020

(86) PCT No.: PCT/IB2020/058865
§ 371 (c)(1),
(2) Date: Mar. 1, 2022

(87) PCT Pub. No.: WO2021/059146
PCT Pub. Date: Apr. 1, 2021

(65) Prior Publication Data

US 2022/0315521 A1 Oct. 6, 2022

(30) Foreign Application Priority Data

Sep. 26, 2019 (IT) ........................ 102019000017330

(51) Int. Cl.
*C07C 209/62* (2006.01)
*C07C 211/60* (2006.01)
*C07C 231/02* (2006.01)

(52) U.S. Cl.
CPC .......... *C07C 209/62* (2013.01); *C07C 231/02* (2013.01); *C07B 2200/07* (2013.01)

(58) Field of Classification Search
CPC . C07C 209/62; C07C 231/02; C07C 2602/08; C07B 2200/07
See application file for complete search history.

(56) References Cited

U.S. PATENT DOCUMENTS

2013/0096174 A1 4/2013 Matsuzaki et al.
2015/0164076 A1 6/2015 Pellacini et al.
2017/0166532 A1* 6/2017 Matsunaga .......... C07D 231/12
2019/0059376 A1 2/2019 Pellacini et al.
2019/0119195 A1 4/2019 Bellandi et al.
2020/0231533 A1 7/2020 Bellandi et al.

FOREIGN PATENT DOCUMENTS

CN 102958367 A 3/2013
CN 104602523 A 5/2015
CN 105992755 A 10/2016
CN 109071439 A 12/2018
(Continued)

OTHER PUBLICATIONS

Y. Gnas, et al, 12 Synthesis, 1899-1930 (2006) (Year: 2006).*
International Search Report issued Oct. 20, 2020 in PCT/IB2020/058865 filed on Sep. 23, 2020.
Combined Taiwanese Office Action and Search Report issued Dec. 14, 2023, in corresponding Taiwanese Patent Application No. 109132887 (with English Translation), 13 pages.
(Continued)

*Primary Examiner* — Alexander R Pagano
*Assistant Examiner* — Frank S. Hou
(74) *Attorney, Agent, or Firm* — Oblon, McClelland, Maier & Neustadt, L.L.P.

(57) ABSTRACT

A process for preparing 1,1,3-trimethylindan-4-amine of formula (I), or a salt thereof, enriched in one of its two enantiomers, in particular the (R) enantiomer, (I)

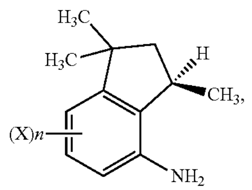

including chirally separating an optionally substituted 2,2,4-trimethyl-1,2,3,4-tetrahydroquinoline of formula (III)

(III)

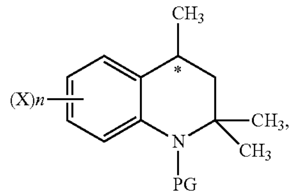

A process may prepare one or more optically active amides of formula (II)

(II)

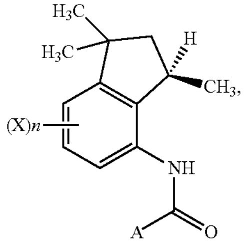

starting from compounds of formula (I).

17 Claims, No Drawings

(56) References Cited

FOREIGN PATENT DOCUMENTS

| | | | | | |
|---|---|---|---|---|---|
| EP | 0 654 464 | A1 | | 5/1995 | |
| EP | 3 103 789 | A1 | | 12/2016 | |
| JP | 7-215921 | A | | 8/1995 | |
| JP | 2012-25735 | A | | 2/2012 | |
| JP | 2015-519384 | A | | 7/2015 | |
| JP | 2019-511524 | A | | 4/2019 | |
| TW | 1337988 | B | | 3/2011 | |
| TW | 201900845 | A | | 1/2019 | |
| WO | WO 2011/162397 | A1 | | 12/2011 | |
| WO | WO 2013/186325 | A1 | | 12/2013 | |
| WO | WO 2015/007897 | A1 | | 1/2015 | |
| WO | WO 2015/118793 | A1 | | 8/2015 | |
| WO | WO-2017160933 | A1 | * | 9/2017 | ............. A01N 37/24 |
| WO | WO 2017/178868 | A1 | | 10/2017 | |

OTHER PUBLICATIONS

Combined Chinese Office Action and Search Report issued May 30, 2023 in Chinese Patent Application No. 202080066657.1 (with English Translation), 21 pages.
Yinhuan et al., "Modern Instrument Analysis", Xi'an Jiaotong University Press, Nov. 2016, 2 pages.
Singapore Office Action issued Jul. 25, 2024 in Singapore Patent Application No. 11202201688Q, 8 pages.
Japanese Office Action issued Jul. 30, 2024 in Japanese Patent Application No. 2022-514528 (with English Translation), 11 pages.
Cliffe et al., "The Acid-catalysed Rearrangement of Tetrahydroquinoline Derivatives", Journal of the Chemical Society C: Organic, Jan. 1, 1996, pp. 514-517.

* cited by examiner

PROCESS FOR PREPARING (R)-4-AMINOINDANE AND CORRESPONDING AMIDES

CROSS-REFERENCE TO RELATED APPLICATIONS

The present application is the national stage of international application PCT/IB2020/058865, filed on Sep. 23, 2020, and claims the benefit of the filing date of Italian Appl. No. 10 2019 000 017 330, filed on Sep. 26, 2019.

The present invention relates to a process for preparing 1,1,3-trimethylindan-4-amine of formula (I), or a salt thereof, enriched in one of its two enantiomers, in particular the enantiomer (R), (I)

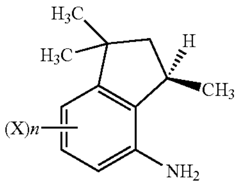

which comprises the chiral separation of an optionally substituted 2,2,4-trimethyl-1,2,3,4-tetrahydroquinoline of formula (III)

(III)

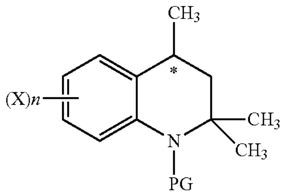

The present invention also relates to a process for preparing optically active amides of formula (II)

(II)

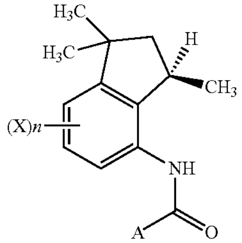

starting from said compounds of formula (I) obtained with the aforesaid preparation process.

BACKGROUND

Indane derivatives bearing an amino group in position 4 as well as the corresponding amides thereof and related preparation processes have been widely described in the literature, such as in JP1070479, JP1117864, JP1313402, JP2157266, JP2249966, JP3077381, JP62096471, EP199822, EP256503, EP276177, EP280275, EP569912, U.S. Pat. Nos. 5,093,347, 5,521,317, WO01/53259, WO2004/018438, WO2004/039789, WO2004/072023, WO2004/103975, WO2005/075452, WO2011/162397, WO2012/084812, WO2013/186325, WO2015/118793 and WO2017/178868.

Amides of said indane derivatives possess, in particular, high fungicidal activity and can therefore be used for the control of phytopathogenic fungi in agricultural crops.

However, few processes are known in the art in which the preparation of 4-aminoindanes in optically active form is provided.

U.S. Pat. No. 5,521,317 reports a process for preparing an enantiomerically enriched 4-aminoindane in four steps, as reported in Scheme 1: i) a condensation reaction between a dihydroquinoline and a derivative of a carboxylic acid bearing a chiral centre (indicated with * in the scheme below) and an LG leaving group; ii) catalytic hydrogenation to provide the corresponding tetrahydroquinoline; iii) addition of a strong acid to obtain the aminoindane derivative; and iv) hydrolysis of the amide bond.

Scheme 1

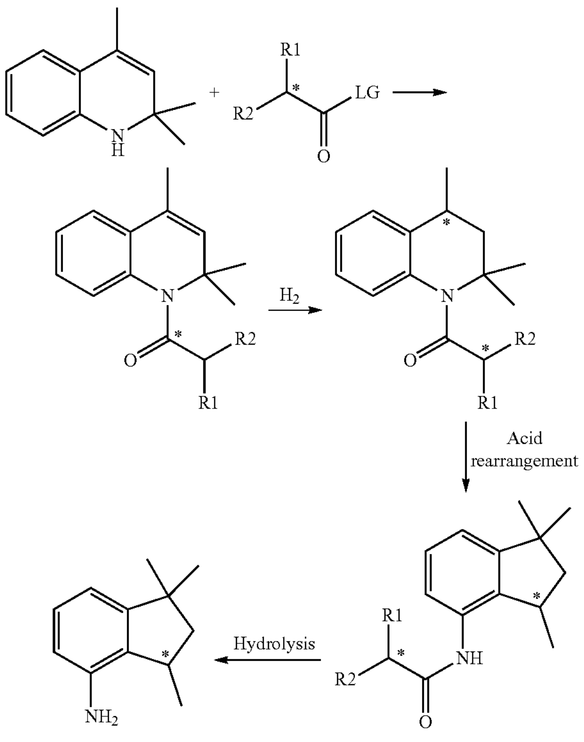

However, this process is not satisfactory from an industrial point of view as it requires the use of a different solvent for each step of the synthesis process, thus increasing the processing and purification required at the end of each reaction. In addition, since the acylated dihydroquinoline and the corresponding tetrahydroquinoline are poorly soluble in non-polar solvents, it is necessary to carry out the hydrogenation reaction at high temperatures which can lead to a racemization of the chiral centre. Consequently, this strategy of introducing the chiral centre generally leads, after numerous purifications, to mixtures enriched in one of the two enantiomers, without however reaching high optical purities.

Patent application WO2011/162397 describes a process for obtaining a mixture enriched with the enantiomer (R) of 4-aminoindane in an 80/20 ratio with respect to the corresponding enantiomer (S). This preparation can be carried out by using a chiral column or through the formation of diastereoisomeric salts with tartaric acid. The separation of enantiomers through the formation of salts with optically active organic acids allows reaching a high optical purity generally only after a certain number of fractional crystallizations, thus involving elaborate operations and a considerable loss of yield.

Moreover, this methodology is applicable only for compounds bearing a free amino group capable of forming the salt with the organic acid added to the reaction mixture.

Furthermore, the separation of the two enantiomers of 4-aminoindane occurs on the final compound of the synthesis, i.e. on a compound obtained after numerous synthetic steps, with a consequent increase in costs due to the loss of material with high added value.

The need is therefore felt for a new process that can be easily industrialized, which allows to obtain a 1,1,3-trimethylindan-4-amine enriched in one of its two enantiomers with high purity and greater synthetic efficiency, in particular the enantiomer (R) which, as is known, is more effective than the enantiomer (S) as a fungicide in agricultural crops.

DESCRIPTION

The Applicant has now surprisingly discovered that it is possible to overcome the aforesaid drawbacks of the state of the art if in a synthesis process of 4-aminoindane the optical resolution of a racemic mixture of a synthesis intermediate of said compound, rather than of the final product, is carried out and subsequently the synthesis is continued on only one of the two enantiomers of said intermediate. In particular, the optical resolution step is carried out on an intermediate compound such as optionally substituted 2,2,4-trimethyl-1,2,3,4-tetrahydroquinoline. The enantiomer of interest, i.e. the enantiomer (R) of the intermediate, is then subjected to an acid rearrangement reaction and to hydrolysis to obtain the final 4-aminoindane compound, which is then enriched in the enantiomer (R).

In accordance with the present invention, it is possible to obtain the enantiomerically enriched 4-aminoindane compound, i.e. a 4-aminoindane compound in which the enantiomer (R) is present in a preponderant amount with respect to the enantiomer (S), with high yields and higher optical purity than what can be obtained with the processes of the prior art.

Therefore, in accordance with a first aspect, the present invention concerns a process for preparing the enantiomer (R) of the compound 1,1,3-trimethylindan-4-amine of formula (I), or a salt thereof, (I)

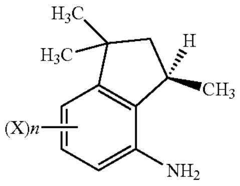

which comprises the following steps:

a) providing a racemic mixture of the optionally substituted 2,2,4-trimethyl-1,2,3,4-tetrahydroquinoline compound of formula (IIIa)

(IIIa)

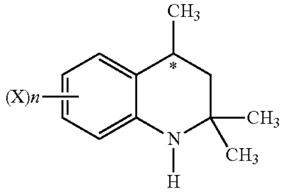

comprising the enantiomer (R) of formula (IVa) and the enantiomer (S) of formula (Va)

(IVa)

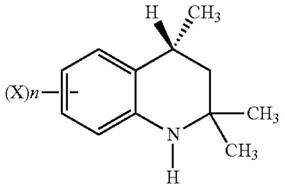

(Va)

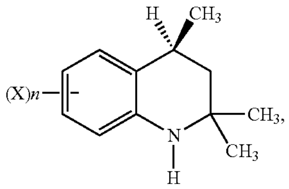

b) treating said racemic mixture of the compound of formula (IIIa) according to an operating sequence A or an operating sequence B, wherein:

the operating sequence A comprises:

b1) converting by means of a protection reaction the racemic mixture of the compound of formula (IIIa) into a racemic mixture of the compound of formula (IIIb) having a protective PG group to protect the nitrogen atom (IIIb)

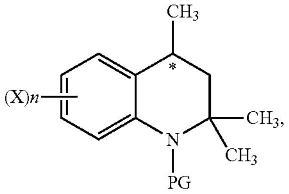

said racemic mixture of the compound of formula (IIIb) comprising the enantiomer (R) of formula (IVb) and the enantiomer (S) of formula (Vb)

(IVb)

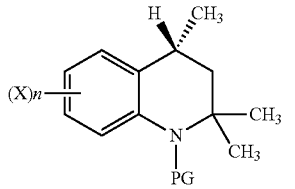

(Vb)

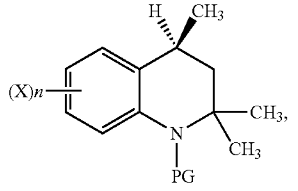

b2) separating said enantiomer (R) of formula (IVb) from said enantiomer (S) of formula (Vb);

the operating sequence B comprises:

b3) separating said enantiomer (R) of formula (IVa) from said enantiomer (S) of formula (Va);

b4) converting said enantiomer (R) of formula (IVa) into an enantiomer (R) of formula (IVb);

c) subjecting said enantiomer (R) of formula (IVb) obtained in step b2 or in step b4 to an acid rearrangement reaction to form the compound of formula (VI)

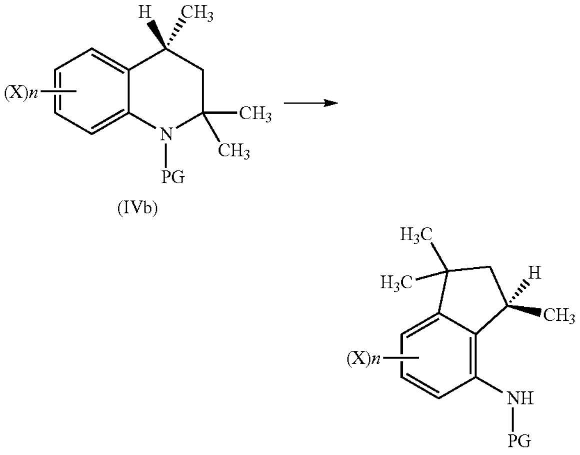

(IVb)

(VI)

d) substituting the PG group of said compound of formula (VI) with a hydrogen atom to obtain the enantiomer (R) of the compound of formula (I);

where in the aforesaid formulas:

* indicates an asymmetric carbon atom;

X is a halogen atom;

n is an integer selected from: 0, 1, 2 and 3;

PG is a —$COR^1$ group or a —$COOR^2$ group, $R^1$ represents a linear or branched $C_1$-$C_6$ alkyl group;

$R^2$ represents a linear or branched $C_1$-$C_6$ alkyl group or a benzyl group.

Examples of $C_1$-$C_6$ alkyl groups are: methyl, ethyl, propyl, butyl, pentyl, hexyl, as well as the relative branched groups.

Examples of halogen atoms are: bromine, chlorine, fluorine, iodine.

In the following of the present description, the process according to the present invention will be described with particular reference to obtaining the final product of formula (I) enriched in the enantiomer (R). However, as will be evident to the person skilled in the art, the same process can be used with the same advantages to obtain 1,1,3-trimethylindan-4-amine enriched in the enantiomer (S), for this purpose it is sufficient to subject the enantiomer (S) of formula (Vb) obtained in step b2 for treating the racemic mixture of the compound of formula (IIIa) to the step c of acid rearrangement. Said enantiomer (S) of formula (Vb) can in turn be obtained by conversion of the unprotected tetrahydroquinoline of formula (Va) or by separation of the enantiomers of the racemic mixture (IIIb) containing the protective PG group of nitrogen.

The tetrahydroquinoline of formula (IIIa), in the form of a racemic mixture, to be fed to step a of the process can be obtained by means of synthetic methods well known to the person skilled in the art, such as for example those described in WO2013/186325 e WO2017/178868, herein incorporated by reference.

The compounds of formula (IIIb), (IVb) and (Vb), in which a protective group PG of formula —$COR_1$ or —$COOR_2$ is present in substitution of the amino hydrogen atom to protect the nitrogen atom from an undesirable reaction and/or allow a reaction to occur on another portion of the molecule, can be obtained by converting the corresponding compounds of formula (IIIa), (IVa) and (Va) by means of a protection reaction, as is known to the person skilled in the art. Methods for introducing and removing protective groups from a molecule are described for example in Theodora W. Greene "Protective Groups in Organic Synthesis" Third Edition.

In accordance with the present invention, starting from the racemic mixture of general formula (IIIa) the enantiomer (R) of general formula (IVb) is obtained, in which the nitrogen protecting group is present. The enantiomer (R) of formula (IVb) can be obtained by applying two different synthesis operating sequences, herein called, respectively, operating sequence A and operating sequence B.

In accordance with the operating sequence A, the racemic mixture of formula (IIIa) is first converted, by means of a protection reaction, into a racemic mixture (IIIb) in which both the enantiomers (R) and (S) have the nitrogen atom protected by the PG group, which has substituted the free hydrogen of the amino group of the compound of formula (IIIa). Subsequently, the racemic mixture of formula (IIIb) is separated into the two enantiomers of formula (IVb) and (Vb) to isolate and recover the enantiomer (R) of interest of formula (IVb).

In an embodiment, for example in step b2, said tetrahydroquinoline of formula (IIIb) in racemic form is subjected to chiral separation preferably by means of a chromatographic technique with a chiral column (e.g. high pressure chromatography (HPLC)) so as to provide the two separate enantiomers (R) and (S) of formula (IVb) and (Vb). The operating sequence A is schematically described in the following Scheme 2.

Scheme 2 - Operating sequence A

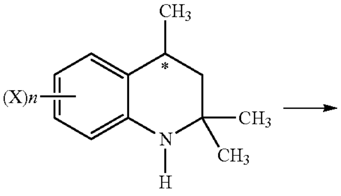

IIIa

-continued

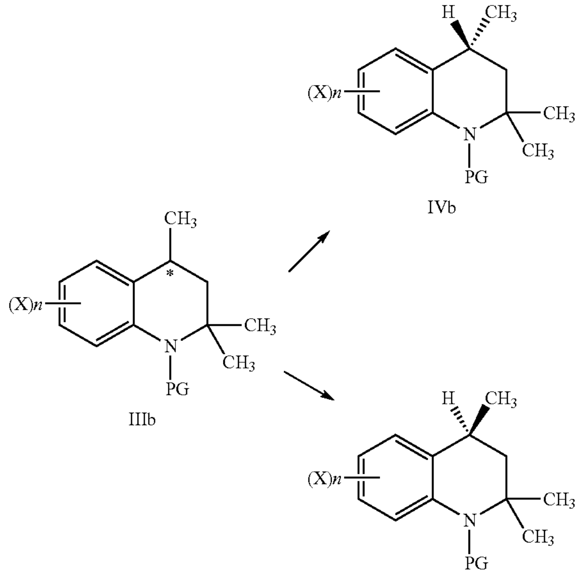

IVb

IIIb

IVa

According to the invention, the racemic tetrahydroquinolines of formula (IIIb) are particularly preferred, wherein:

X is a hydrogen or fluorine atom;

n is equal to 1;

PG is an acetyl group, a tert-butoxycarbonyl group or a carbobenzyloxy group.

In accordance with the operating sequence B, the racemic mixture of formula (IIIa) is first separated into the two enantiomers of formula (IVa) and (Va) to isolate and recover the enantiomer (R) of interest of formula (IVa). Subsequently, the enantiomer (R) of formula (IVa) is converted, by means of a protection reaction, into the corresponding protected enantiomer (R) of formula (IVb) containing a PG group to protect the nitrogen atom. The operating sequence B is schematically described in the following Scheme 3.

Scheme 3 - Operated sequence B

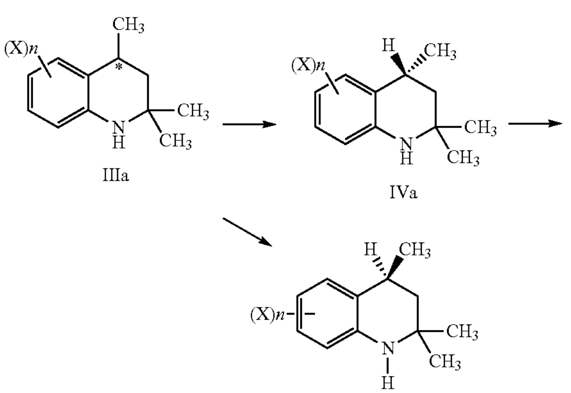

IIIa

IVa

Va

-continued

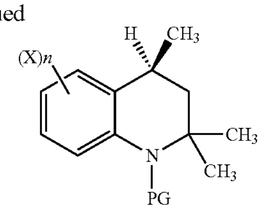

IVb

The separation of the two enantiomers of formula (IVa) and (Va) in step b3 can be achieved by chromatographic separation on a chiral column.

In this case, since the enantiomers of the racemic mixture (IIIa) possess an unprotected amino group, the two enantiomers of formula (IVa) and (Va) can also be effectively separated through formation of chiral salts with a suitable chiral acid and subsequent basic hydrolysis so as to give the desired enantiomer. In this case, the separation step b3 can comprise for example the following steps:

reacting the racemic mixture of formula (IIIa) with an optically active acid to obtain a mixture of a corresponding enantiomeric salt (R) and a corresponding enantiomeric salt (S);

separating said enantiomeric salt (R) from said enantiomeric salt (S);

subjecting at least said enantiomeric salt (R) to basic hydrolysis to obtain said enantiomeric compound (R) of formula (IVa) to be fed to the subsequent steps of the process.

Preferably, in step b3 of separation of the two enantiomeric salts, the chiral resolution is carried out by high pressure chromatography (HPLC) on a chiral column.

Preferably, the compound of formula (IIIa) or (IIIb) is dissolved in at least one polar or non-polar organic solvent, or in a mixture thereof.

Preferred examples of polar solvents are: ethanol, isopropanol, acetonitrile, tetrahydrofuran, dioxane or mixtures thereof.

Preferred examples of non-polar solvents are: hexane, heptane, toluene or mixtures thereof.

Preferably, the tetrahydroquinoline of formula (IIIa) or (IIIb) is dissolved in a mixture of solvents, comprising at least one polar organic solvent and at least one non-polar organic solvent.

More preferably, said at least one polar organic solvent is isopropanol and said at least one non-polar organic solvent is heptane.

For the purposes of the present description and the attached claims, the term "heptane" refers both to n-heptane and to a mixture of isomers.

In the aforesaid mixture of solvents, the polar solvent and the non-polar solvent are present in a volume ratio preferably comprised between (80:20) and (100:0), more preferably between (90:10) and (99.5:0.5), even more preferably about (99:1). In one embodiment, the resolution of the two enantiomers is achieved by interacting the solution of the racemic compound of formula (IIIa) (obtained in step a) or (IIIb) (obtained in step b1) with a commercial chiral stationary step according to the modality of high-pressure preparative liquid chromatography (HPLC), eluting said solution using a mobile phase.

Preferably, said mobile phase is a mixture of at least one polar solvent and at least one non-polar solvent. More preferably, said at least one polar solvent is isopropanol and said at least one non-polar solvent is heptane.

According to a preferred embodiment, said mobile phase has the same chemical composition as the solvent used to prepare the solution containing the tetrahydroquinoline of formula (IIIa) or (IIIb). For example, said mobile phase can be a mixture (99:1) of isopropanol and heptane.

The different and selective interaction between the stationary phase and the single enantiomers of formula (IVa) and (Va) of the racemic mixture (IIIa) or (IVb) and (Vb) of the racemic mixture (IIIb) allows the separation of the same and their isolation in two distinct fractions.

At the end of the contact with the stationary phase, the individual isomers are collected in two distinct solutions and possibly recovered by evaporation of the respective solvents.

The separation operations described above allow to isolate each of the isomers (IVa) and (Va) (obtained in step b3) or (IVb) and (Vb) (obtained in step b2) with a high degree of purity. In fact, each of the separated isomers contains relatively low amounts of the other isomer. In each separate fraction, the molar ratio between the two isomers is preferably comprised between (80:20) and (100:0), more preferably between (90:10) and (99.5:0.5), even more preferably about (99:1).

The optical purity of the enantiomers of formula (IVa) and (Va) or (IVb) and (Vb) thus obtained is greater than 90% of enantiomeric excess (ee), preferably greater than 98% ee, more preferably greater than 99% ee.

The enantiomeric excess ee expresses the greater amount of an enantiomer than the other one in a mixture of the two enantiomers; the ee value is calculated using the formula $[(E_1-E_2)/(E_1+E_2)*100]$, where $E_1$ and $E_2$ are the molar fractions of the two enantiomers.

According to the invention, once the two isomers have been isolated, the isomer of interest, that is the isomer (R) having formula (IVb), in step c is subjected to a rearrangement reaction of the bonds in an acid environment to provide the corresponding indane of formula (VI), as reported for example in scheme 4 below.

Scheme 4

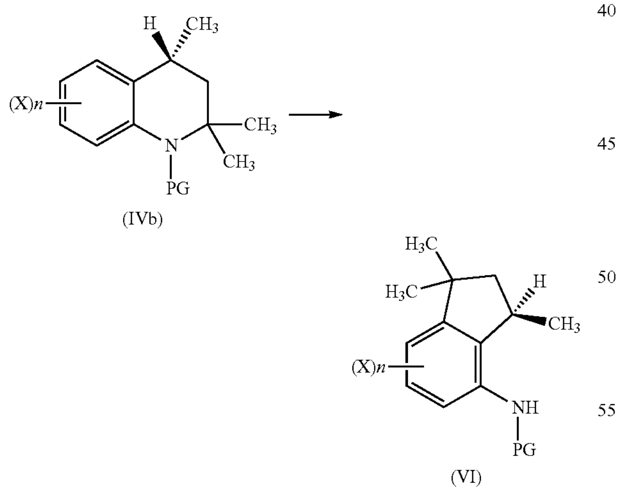

(IVb)

(VI)

The acid environment that allows to obtain the indane of formula (VI) can be obtained by adding an organic or inorganic acid to the solution containing the isomer (R) of formula (IVb).

Preferably, an inorganic acid is added, more preferably said inorganic acid is selected from orthophosphoric acid and sulfuric acid, even more preferably said acid is sulfuric acid.

Said organic or inorganic acid is added to the reaction mixture in an amount comprised between 3 and 10 molar equivalents, preferably between 4 and 9 molar equivalents, more preferably between 6 and 7 molar equivalents, with respect to the compound of formula (IVb).

Preferably, the acid is added in the form of an aqueous solution in which the acid concentration is comprised between 80% and 98% by weight, more preferably between 90% and 97% by weight.

Furthermore, since the addition of acid is followed by heat development, it is preferable to control the temperature of the reaction mixture.

For this purpose, the reaction is preferably carried out at a temperature comprised in the interval between 10° C. and 60° C., more preferably between room temperature (20° C.) and 40° C.

Preferably, the reaction mixture is kept under stirring for a time comprised between 10 and 30 hours, more preferably between 15 and 25 hours, even more preferably for about 20 hours, so as to obtain a substantially complete conversion of the tetrahydroquinoline of formula (IVb) into the corresponding indane of formula (VI).

As is well known to person skilled in the art, the addition of acid or base to a reaction mixture containing a chiral compound can lead to a partial or complete racemization of the chiral centre.

The Applicant has now found that the acid rearrangement reaction of step c does not cause a substantial racemization of the chiral centre of the isomer subjected to the reaction, thus being able to obtain an indane derivative of formula (VI) and therefore a final compound of formula (I) having substantially the same optical purity as the tetrahydroquinoline of formula (IVb) fed to the acid rearrangement step.

In accordance with the present invention, the optical purity of the indane of formula (VI) is preferably greater than 97% ee, more preferably greater than 99% ee, even more preferably greater than 99.5% ee.

In step d the compound of formula (VI) is subjected to a deprotection reaction to provide the desired isomer (R) of the compound of formula (I), preferably with an unchanged optical purity, i.e. with an ee greater than 97%, preferably greater than 99%, more preferably greater than 99.5%.

The reaction conditions of the aforesaid deprotection reaction can be selected on the basis of the composition of the protective PG group.

For example, when the PG group is a $—COR_1$ group, wherein $R_1$ is a methyl, the deprotection reaction can be a hydrolysis reaction in an acid environment, preferably in the presence of an inorganic acid, more preferably sulfuric acid.

When the PG group is a $—COOR_2$ group, wherein $R_2$ is a benzyl, the deprotection reaction of the compound of formula (VI) can be a catalytic hydrogenation reaction in order to obtain the desired amino group of indane of formula (I).

The process of the present invention, thanks to the realization of the chiral resolution of the racemic mixture of an intermediate compound used as synthesis precursor, allows to obtain the compound 1,1,3-trimethylindan-4-amine with a preponderant presence of the desired isomer (R), with a higher selectivity and efficiency with respect to the processes of the prior art.

Preferably, the process according to the present invention is used to obtain the compound of formula (I) enriched in the enantiomer (R), said enantiomer having a higher fungicidal activity than that of the enantiomer (S).

Furthermore, the Applicant has found that it is possible to use the isomer (S) which is not fed to step c of acid rearrangement, i.e. the isomer (S) of the compound of formula (Vb) or the isomer (S) of the compound of formula (Va), to again obtain a racemic tetrahydroquinoline of formula (IIIa) or (IIIb) to be recycled in the preparation process of the compounds of formula (I) enriched enantiomerically, by means of certain synthetic passages with an excellent yield and purity. This recycling opportunity makes the process according to the present invention particularly advantageous from an industrial point of view.

According to an embodiment, the recycling process provides for the conversion of the enantiomer that has not been subjected to acid rearrangement in step c, that is the isomer (S) of formula (Vb), into the racemic tetrahydroquinoline of formula (IIIb).

The process according to the present invention, when carried out in accordance with the operating sequence A, can therefore comprise, for example, the following steps:

i) oxidizing, by means of an oxidizing agent, the enantiomer (S) of formula (Vb) obtained in step b2 to form the compound of formula (VII)

(VII)

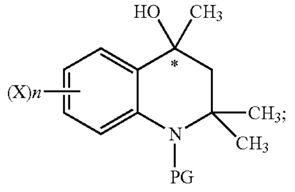

ii) dehydrating said compound of formula (VII) in an acid environment to obtain a compound of formula (VIII)

(VIII)

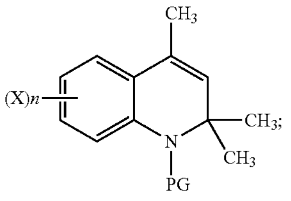

iii) hydrogenating said compound of formula (VIII) to obtain a racemic mixture of the compound of formula (IIIb) comprising the enantiomer (R) of formula (IVb) and the enantiomer (S) of formula (Vb).

The compound of formula (IIIb) can then be recycled at the head of the process, feeding it to step b2.

When made in accordance with the operating sequence B, the isomer to be recycled is the isomer (S) of formula (Va) obtained in step b3. This isomer, before being subjected to steps i-iii, is converted, by means of a protection reaction, into the corresponding protected enantiomer (S), comprising a protective PG group on the nitrogen atom. The presence of the protective PG group on the nitrogen atom serves in particular to avoid undesirable reactions of the nitrogen atom during the oxidation step i.

The process according to the present invention, when carried out in accordance with the operating sequence B, can therefore comprise the following recycling steps in sequence:

converting by means of a protection reaction said enantiomer (S) of formula (Va) obtained in step b3 into an enantiomer (S) of formula (Vb);

i) oxidizing, by means of an oxidizing agent, said enantiomer (S) of formula (Vb) to form the compound of formula (VII)

(VII)

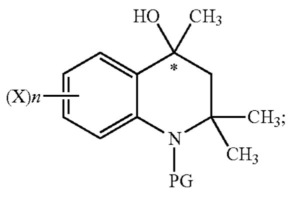

ii) dehydrating said compound of formula (VII) in an acid environment to obtain a compound of formula (VIII)

(VIII)

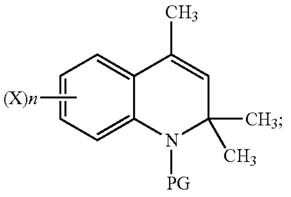

iii) hydrogenating said compound of formula (VIII) to obtain a racemic mixture of the compound of formula (IIIb) containing the enantiomer (R) of formula (IVb) and the enantiomer (S) of formula (Vb).

It is noted that, depending on the nature of the protective PG group, the reaction conditions of step ii) or of step iii) can lead to the partial removal of the protective PG group, and therefore to the formation of mixtures of products comprising also or mainly compounds in which the protective group on the nitrogen has been replaced by a hydrogen atom.

For example, if PG is a group of formula —$COR_1$ (for example an acetyl group), it may happen that the acidity conditions of step ii) cause the deprotection of at least a part of the compounds subjected to the dehydration step with consequent formation of compounds of formula (VIII) in which the protective PG group has been substituted by a hydrogen atom.

If a mixture of compounds of formula (VIII) is obtained in which the nitrogen atom is only partially protected, it is preferable to subject the product leaving step ii to an additional deprotection step (step ii-bis), to obtain a compound of formula (IX) substantially free of protective PG groups.

(IX)

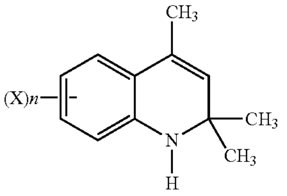

The deprotection step ii-bis can be, for example, a hydrolysis step carried out according to the prior art according to the nature of the protective PG group.

The compound (IX) can then be fed to the hydrogenation step iii to obtain an optionally substituted 1,2,3,4-tetrahydroquinline of formula (IIIa). The compound of formula (IIIa) can be recycled in the production process of the compounds of formula (I), feeding it to step a.

If PG is a group of formula —$COOR_2$ (for example a carbobenzyloxy group), the acidity conditions adopted in step ii are generally not such as to cause deprotection of the compounds subjected to dehydration, so that the compound of formula (VIII) leaving step ii still possesses the protective PG group on the nitrogen atom. However, this group can be subjected to removal in the subsequent step iii of hydrogenation of the compounds of formula (VIII). In this case, step iii leads to obtaining compounds of formula (IIIa), which can be recycled at the head of the process, feeding them to step a.

Preferably, the compound fed to the recycling step i is dissolved in at least one polar organic solvent.

Preferred examples of polar solvents are: acetonitrile, acetone, dioxane or mixtures thereof.

According to a preferred aspect of the invention, the compound fed to step i is dissolved in acetonitrile.

The oxidizing agent is added to the solution of the compound of formula (Vb) in an amount comprised between 3 and 10 molar equivalents, preferably between 3 and 5 equivalents, with respect to the moles of the compound of formula (Vb). The oxidizing agent can be used as such in solid form or in the form of an aqueous solution, preferably having a concentration by weight comprised between 5% and 30%, more preferably about 20%.

Examples of oxidizing agents suitable for use in the present invention are: potassium permanganate, hydrogen peroxide, sodium dichromate, potassium peroxymonosulfate (Oxone®) and mixtures thereof.

A preferred oxidizing agent according to the invention is potassium permanganate.

The aforesaid oxidation reaction preferably takes place at a temperature comprised between 25° C. and the boiling temperature of the solvent, more preferably at about the boiling temperature of the solvent. Preferably, the oxidation reaction reaches substantial completion in a time interval comprised between 5 and 10 hours.

The alcohol of formula (VII) obtained from the oxidation reaction can be isolated and purified according to methods well known to the person skilled in the art, such as solvent extraction, acid-base processing, precipitation, crystallization, filtration, chromatography.

In the subsequent recycle step ii), the alcohol of formula (VII) is converted into the corresponding dihydroquinoline of formula (VIII) by means of an elimination reaction of water in an acid environment.

For this purpose, for example, the compound of formula (VII) can be added, preferably in portions, to an aqueous solution of an organic or inorganic acid, preferably inorganic, said acid having a percentage by weight comprised between 20% and 90%, more preferably about 50% by weight.

More preferably, said inorganic acid is sulfuric acid and is used in an amount comprised between 5% and 30% by weight, with respect to the weight of the alcohol having formula (VII).

The water elimination reaction is preferably carried out at a temperature comprised between 15° C. and 40° C., more preferably at a temperature of about 25° C. Preferably, the reaction reaches substantial completeness in a time interval comprised from 4 to 8 hours.

The dihydroquinoline of formula (VIII) obtained at the end of the dehydration can be isolated and purified according to methods well known to the person skilled in the art, such as solvent extraction, acid-base processing, precipitation, crystallization, filtration, chromatography.

In the hydrogenation step iii), the dihydroquinoline of formula (VIII) is preferably dissolved in an organic solvent and a hydrogenation catalyst is added to the solution thus obtained.

Said hydrogenation catalyst is preferably a heterogeneous catalyst, more preferably selected from palladium on carbon, palladium hydroxide on carbon, Raney nickel and platinum oxide, even more preferably it is palladium on carbon.

Examples of solvents that can be used in the hydrogenation reaction are: aliphatic or cycloaliphatic hydrocarbons (e.g. petroleum ether, hexane, cyclohexane, heptane), chlorinated hydrocarbons (e.g. methylene chloride, chloroform, carbon tetrachloride, dichloroethane), aromatic hydrocarbons (e.g. benzene, toluene, xylene, chlorobenzene), alcohols and glycols (e.g. methanol, ethanol, isopropanol, ethylene glycol), esters (e.g. ethyl acetate, butyl acetate) or mixtures thereof.

Preferred solvents according to the present invention are aliphatic hydrocarbons such as hexane and heptane, chlorinated hydrocarbons such as methylene chloride and dichloroethane, alcohols such as methanol, ethanol and isopropanol, toluene, ethyl acetate.

Heptane, dichloroethane, methanol and toluene are particularly preferred.

As is well known to the person skilled in the art, the hydrogenation reaction can be carried out using gaseous hydrogen, at a pressure higher than 1 bar or at atmospheric pressure.

Preferably, the hydrogenation reaction of step iii) is carried out at atmospheric pressure.

At the end of the reaction, the catalyst is filtered and preferably reused for subsequent productions.

The racemic tetrahydroquinoline of formula (IIIb) obtained at the end of step iii) can be isolated from the reaction mixture by techniques well known to the person skilled in the art, for example by evaporation of the solvent.

Preferably, said tetrahydroquinoline of formula (IIIb) is fed again to the head of the process without being previously subjected to purification.

A further object of the present invention is a process for preparing an optically active amide of formula (II), enriched in the enantiomer (R)

(II)

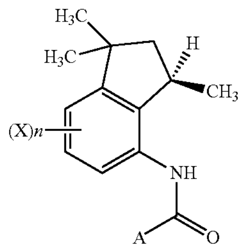

which comprises the following steps:

- preparing a compound 1,1,3-trimethylindan-4-amine of formula (I), or a salt thereof, enriched in the enantiomer (R) according to the process of the present description;
- condensing said compound of formula (I) with at least one compound of formula AC(O)Y, wherein:

A represents a $C_6$-$C_{10}$ aryl group or a heterocyclic group with 5 or 6 terms containing from 1 to 3 heteroatoms selected from N, O, S, said groups being optionally substituted with one or more $R_3$ and $R_4$ groups;

$R_3$ represents a $C_1$-$C_6$ alkyl group or a $C_1$-$C_6$, haloalkyl group, said groups being optionally substituted with one or more groups selected from R', OR', $S(O)_mR'$; or $R_3$ represents a $C_3$-$C_6$ cycloalkyl group, a $C_4$-$C_9$ cycloalkylalkyl group, a $C_2$-$C_6$ alkenyl group, a $C_2$-$C_6$ alkynyl group, a $C_6$-$C_{10}$ aryl group, a $C_7$-$C_{12}$ arylalkyl group or a heterocyclic group with 5 or 6 terms containing from 1 to 3 heteroatoms selected from N, O, S, said groups being optionally substituted with one or more groups selected from a halogen atom, R', OR', NR'R", $S(O)_mR'$, CONR'R", COR', $CO_2R'$, CN, $NO_2$;

$R_4$ represents a $C_1$-$C_6$ alkyl group or a $C_1$-$C_6$, haloalkyl group, said groups being optionally substituted with one or more groups selected from R', OR', $S(O)_mR'$; or $R_4$ represents a $C_3$-$C_6$ cycloalkyl group, a $C_4$-$C_9$ cycloalkylalkyl group, a $C_6$-$C_{10}$ aryl group or a $C_7$-$C_{12}$ arylalkyl group, said groups being optionally substituted with one or more groups selected from a halogen atom, R', OR', NR'R", $S(O)_mR'$, CONR'R", COR', $CO_2R'$, CN, $NO_2$;

R' and R", equal or different from each other, represent a hydrogen atom, a $C_1$-$C_4$ alkyl group or a $C_1$-$C_4$ haloalkyl group;

Y represents a hydroxyl group, a halogen atom, a $C_1$-$C_6$, alkoxy group, a $C_1$-$C_6$ alkylsulfonyloxy group or a $C_6$-$C_{10}$, arylsulfonyloxy group, said $C_1$-$C_6$ alkoxy, $C_1$-$C_6$ alkylsulfonyloxy and $C_6$-$C_{10}$ arylsulfonyloxy groups being optionally substituted with one or more halogen atoms;

m is an integer selected from: 0, 1, 2 and 3.

Examples of $C_1$-$C_6$ alkyl groups are: methyl, ethyl, propyl, butyl, pentyl, hexyle.

Examples of $C_1$-$C_6$ haloalkyl groups are: dichloromethyl, difluoromethyl, trichloromethyl, trifluoromethyl, chlorodifluoromethyl, dichloroethyl, trifluoroethyl, tetrafluoroethyl, pentafluoroethyl, tetrafluoropropyl, pentafluoropropyl, dichlorobutyl, difluorobutyl, dichloropentyl, difluoropentyl, dichlorohexyl, difluorohexyl.

Examples of $C_3$-$C_6$ cycloalkyl groups are: cyclopropyl, cyclobutyl, cyclopentyl, cyclohexyl.

Examples of $C_4$-$C_9$ cycloalkylalkyl groups are: cyclopropylmethyl, cyclobutylmethyl, cyclopentylmethyl, cyclohexylmethyl, cyclohexylethyl, cyclohexylpropyl.

Examples of $C_2$-$C_6$ alkenyl groups are: ethenyl, propenyl, butenyl, pentenyl, hexenyl.

Examples of $C_2$-$C_6$ alkynyl groups are: ethinyl, propinyl, butinyl, pentinyl, hexinyl.

Examples of $C_6$-$C_{10}$ aryl groups are: phenyl, naphthyl.

Examples of $C_7$-$C_{12}$ arylalkyl groups are: benzyl, phenylethyl, phenylpropyl, phenylbutyl, phenylpentyl, phenylhexyl, naphthylmethyl, naphthylethyl.

Examples of heterocyclic rings with 5 or 6 terms containing from 1 to 3 heteroatoms selected from N, O, S are: pyrrolyl, pyrazolyl, imidazolyl, triazolyl, thiadiazolyl, oxadiazolyl, furanyl, thiophenyl, pyridyl, pyrimidyl, triazinyl.

Examples of nitrogenous heterocyclic rings with 5 or 6 terms are: pyrrolidyl, piperidyl, morpholyl.

Examples of halogen atoms are: fluorine, chlorine, bromine, iodine.

Among the optically active amides of formula (II) enriched enantiomerically which can be prepared with the process of the present invention, the preferred ones are those in which:

A represents one of the following $A_1$-$A_5$ heterocyclic groups:

$A_1$

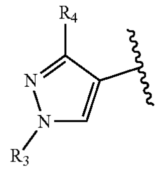

$A_2$

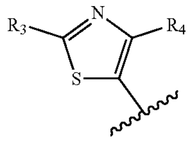

$A_3$

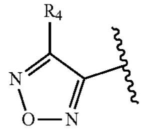

$A_4$

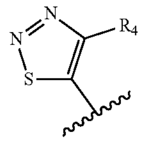

$A_5$

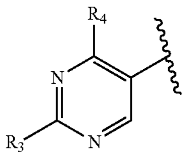

$R_3$ represents a $C_1$-$C_6$ alkyl group, a $C_1$-$C_6$ haloalkyl group or a phenyl optionally substituted with halogen atoms, $C_1$-$C_4$ alkyl groups, $C_1$-$C_4$ haloalkyl group, $C_1$-$C_4$ alkoxy groups, $C_1$-$C_4$ haloalkoxy groups;

$R_4$ represents a $C_1$-$C_6$ alkyl group, a $C_1$-$C_6$ haloalkyl group or a phenyl optionally substituted with halogen atoms, $C_1$-$C_4$ alkyl groups, $C_1$-$C_4$ haloalkyl group, $C_1$-$C_4$ alkoxy groups, $C_1$-$C_4$ haloalkoxy groups;

Particularly preferred are the products of formula (II) wherein:

$R_3$ represents a $C_1$-$C_6$ alkyl group or a phenyl optionally substituted with halogen atoms;

$R_4$ represents a methyl, a difluoromethyl, a trifluoromethyl or a phenyl optionally substituted with halogen atoms.

Even more preferred are the products of formula (II) wherein:

A represents $A_1$;

$R_3$ represents a methyl;

$R_4$ represents a methyl, a difluoromethyl or a trifluoromethyl.

In one embodiment, in the condensation step, a derivative of a carboxylic acid AC(O)Y is added to the 4-aminoindane solution of formula (I) obtained in step d of the preparation process of the compounds of formula (I). Said solution is preferably used as it is for the preparation of aminoindane amides of formula (II), i.e. without being previously purified.

Said derivative of an carboxylic acid AC(O)Y is preferably added in a molar ratio comprised between 0.9 and 1.1, more preferably between 0.95 and 1.05, even more preferably in an equimolar amount with respect to the amount of 4-aminoindane of formula (I).

Preferably, said derivative of a carboxylic acid of formula AC(O)Y is a chloride of a carboxylic acid, i.e. Y represents a chlorine atom.

After the addition of the derivative of formula AC(O)Y, the reaction mixture is brought to a temperature comprised between 60° C. and the reflux temperature of the hydrocarbon solvent, preferably between 95° C. and 100° C. At the end of the condensation reaction, the reaction mixture can be cooled and an alkaline aqueous solution added in order to neutralize the residual acidity.

In another embodiment, after the addition of the derivative of formula AC(O)Y, the reaction mixture is stirred at room temperature in an inert atmosphere (e.g. nitrogen) for a time in the interval from 1 to 30 hours in the presence of an organic base, such as for example triethylamine, diisopropylamine or pyridine. At the end of the condensation reaction, the reaction mixture can be cooled and an acidic aqueous solution added in order to neutralize the residual alkalinity.

The amide derivative of formula (II) thus formed can be subsequently isolated and purified according to techniques well known to the person skilled in the art, for example, by precipitation, filtration and washing of the solid product.

The fact that the final amide can be isolated by filtration from the reaction mixture represents a further advantage of the present invention with respect to the processes known in the art.

As mentioned above, in the preparation process of the compounds of formula (I) according to the present invention, the high optical purity of the compound of formula (I) is substantially maintained even at the end of step c of acid rearrangement, thanks to the fact that the specific experimental conditions do not lead to a partial or complete racemization of the chiral centre.

Furthermore, the Applicant has also found that after the condensation step of the 4-aminoindane of formula (I) with the compound of formula AC(O)Y, the optical purity of the final amide of formula (II) remains substantially unchanged with respect to that of the tetrahydroquinoline of formula (IVb), i.e. it is preferably greater than 97% ee, more preferably greater than 99% ee, even more preferably greater than 99.5% ee.

For the purpose of better illustrating the invention, the following examples are now provided, which are to be considered illustrative and non-limiting examples thereof.

EXPERIMENTAL PART

Example 1—Operating Sequence A a) Preparation of 1-acetyl-6-fluoro-2,2,4-trimethyl-1,2,3,4-tetrahydroquinoline (TIM)

The compound 1-acetyl-6-fluoro-2,2,4-trimethyl-1,2,3,4-tetrahydroquinoline in racemic form and containing the acetyl group as nitrogen protecting group was prepared and isolated following the procedure described in patent application WO2017/178868.

b) Chiral Separation of Racemic 1-acetyl-6-fluoro-2,2,4-trimethyl-1,2,3,4-tetrahydroquinoline (TIM)

1.7 g of racemic 1-acetyl-6-fluoro-2,2,4-trimethyl-1,2,3,4-tetrahydroquinoline were dissolved in a mixture of n-heptane and isopropyl alcohol (85:15) and subjected to chiral separation by preparative chromatography eluting with a mixture of n-heptane and isopropyl alcohol (99:1). The two enantiomers were obtained after evaporation of the solvents under reduced pressure: 0.84 g of (4R)-1-acetyl-6-fluoro-2,2,4-trimethyl-1,2,3,4-tetrahydroquinoline (IVb) (100% e.e; yield=50%) and 0.84 g of (4S)-1-acetyl-6-fluoro-2,2,4-trimethyl-1,2,3,4-tetrahydroquinoline (Vb) (99.96% e.e.).

c) Preparation of N-[(3R)-7-fluoro-1,1,3-trimethyl-indan-4-yl}acetamide (VI)

The (4R)-acetyl-tetrahydroquinoline (IVb) (0.80 g, 3.40 mmol) is slowly added, in portions, to a solution of concentrated sulfuric acid at 93% by weight (3.58 g, 35.0 mmol), maintaining the temperature between 15° C. and 20° C. The mixture is then heated to 34-36° C. for 20 hours, under vigorous stirring.

A solution containing N-[(3R)-7-fluoro-1,1,3-trimethyl-indan-4-yl}acetamide (VI) (100% e.e.) is thus obtained.

d) Preparation of (3R)-7-fluoro-1,1,3-trimethylindan-4-ylamine (I)

The solution of N-[(3R)-7-fluoro-1,1,3-trimethylindan-4-yl}acetamide (VI) is diluted with water (3.50 g) until a sulfuric acid concentration equal to about 50% by weight is reached.

The reaction mixture is heated at 110-115° C. for 10-12 hours.

Subsequently, it is cooled to room temperature and the mixture is first diluted with water (3.50 g) and then basified up to pH=12 with an aqueous solution of sodium hydroxide at 10% by weight.

Dichloromethane (20 mL) is added to the alkaline solution, the phases are separated and the aqueous phase is re-extracted with dichloromethane (20 mL). The combined organic phases are washed with water and dried over sodium sulphate.

The solvent is evaporated under reduced pressure obtaining 0.58 g of (3R)-7-fluoro-1,1,3-trimethylindan-4-ylamine (I) (100% e.e.; yield starting from (4R)-acetyl-tetrahydroquinoline (IV)=88.3%; overall yield starting from racemic acetyl-tetrahydroquinoline=44.0%).

Example 2 a) Preparation of 3-difluoromethyl-N-[(3R)-7-fluoro-1,1,3-trimethyl-4-indanyl]-1-methyl-4-pyrazolecarboxamide (II)

The chloride of the 3-difluoromethyl-1-methyl-1H-pyrazole-4-carboxylic acid (0.58 g, 3.0 mmol), obtained according to known organic chemistry procedures is added to a solution of the enantiopure isomer (3R)-7-fluoro-1,1,3-trimethylindan-4-ylamine (I) (0.58 g, 3.0 mmol) in heptane (11 mL), heated to 50° C. The addition of the chloride of the acid takes place by dripping in about ten minutes with the formation of a precipitate. The reaction mixture is heated under reflux (internal 95-97° C.) with gas HCl evolution. After 4 hours, the reaction is finished, the mixture is cooled to room temperature and basified to pH=8-10 with an aqueous solution of sodium hydroxide at 2.5% by weight (5 mL).

The precipitate is filtered and the solid obtained is suspended in water (5 mL) at 45° C. and filtered again. The solid is again washed on a filter with water (up to neutral pH) and with heptane (5 mL).

The solid is then dried in an oven at 55° C. under vacuum and 0.99 g of amide (II) are obtained (100% e.e.; yield=94%).

b) Preparation of 3-difluoromethyl-N-[(3R)-7-fluoro-1,1,3-trimethyl-4-indanyl]-1-methyl-4-pyrazolecarboxamide (II) (Alternative Method)

A solution in dichloroethane (6.0 mL) of the chloride of the 3-difluoromethyl-1-methyl-1H-pyrazole-4-carboxylic acid (0.66 g, 3.4 mmol), obtained according to known procedures of organic chemistry, is added to a solution of the enantiopure isomer (3R)-7-fluoro-1,1,3-trimethylindan-4-ylamine (I) (0.66 g, 3.4 mmol), triethylamine (0.42 g, 4.1 mmol) and 4-dimethylamino pyridine (catalytic amount) in dichloroethane (5.0 mL). The addition of the chloride of the acid takes place by dripping in about ten minutes. The reaction mixture is stirred at room temperature in an inert atmosphere. After 18 hours, the reaction is finished, the mixture is cooled to 0-5° C. and acidified with an aqueous solution of hydrochloric acid at 5% by weight (20 mL).

The phases are separated and the organic phase is washed respectively with: 5% hydrochloric acid (2 times with 20 mL), water (2 times with 20 mL) and brine. The organic solvent is evaporated under reduced pressure and the raw obtained purified by chromatography (eluent: heptane/ethyl acetate 6:4) obtaining 1.1 grams of the amide (II) (100% e.e.; yield=92%).

Example 3 a) Preparation of 1-acetyl-6-fluoro-4-hydroxy-2,2,4-trimethyl-1,2,3,4-tetrahydroquinoline (VII)

A solution of 0.80 g of (4S)-1-acetyl-6-fluoro-2,2,4-trimethyl-1,2,3,4-tetrahydroquinoline (Vb) (3.40 mmol) in acetonitrile (10 mL) is refluxed and an aqueous solution of $KMnO_4$ at 20% by weight (17.0 mmol) is dripped slowly in 5 hours, keeping the mixture under reflux and vigorous stirring. At the end of the dripping, the mixture is allowed to reflux for three hours.

Thereafter, it is cooled to room temperature and isopropanol (1.0 mL) is added while continuing to stir for one hour.

The heterogeneous mixture is filtered on celite to eliminate the salts, washing the filter with ethyl acetate and water.

The phases are separated and the aqueous phase is re-extracted with ethyl acetate. The combined organic phases are washed with brine and dried over sodium sulphate. The solvent is evaporated under reduced pressure obtaining 0.76 grams of 1-acetyl-6-fluoro-4-hydroxy-2,2,4-trimethyl-1,2,3,4-tetrahydroquinoline (VII).

b) Preparation of 1-acetyl-6-fluoro-2,2,4-trimethyl-1,2-dihydroquinoline (VIII)

A solution of sulfuric acid concentrated at 50% by weight (5.0 mL) is slowly added to 1-acetyl-6-fluoro-4-hydroxy-2,2,4-trimethyl-1,2,3,4-tetrahydroquinoline of formula (VII) (0.76 grams, 3.0 mmol). The mixture is then stirred at room temperature for four hours.

A solution containing 1-acetyl-6-fluoro-2,2,4-trimethyl-1,2-dihydroquinoline (VIII) is thus obtained.

c) Preparation of 6-fluoro-2,2,4-trimethyl-1,2-dihydroquinoline (IX)

Since the compound of formula (VIII) obtained in the previous step b may contain at least in part compounds of formula (VIII) without the acetyl protecting group, the following deprotection step is carried out in order to obtain a compound substantially of formula (IX).

The 1-acetyl-6-fluoro-2,2,4-trimethyl-1,2-dihydroquinoline solution (VIII) is heated to 110-115° C. for 10-12 hours.

Subsequently, it is cooled to room temperature and the mixture is first diluted with water (3.50 g) and then basified up to pH=12 with an aqueous solution of sodium hydroxide at 10% by weight.

Dichloromethane (20 mL) is added to the alkaline solution, the phases are separated and the aqueous phase is re-extracted with dichloromethane (20 mL). The combined organic phases are washed with water and dried over sodium sulphate.

The solvent is evaporated under reduced pressure obtaining 0.51 g of 6-fluoro-2,2,4-trimethyl-1,2-dihydroquinoline (IX).

d) Preparation of 6-fluoro-2,2,4-trimethyl-1,2,3,4-tetrahydroquinoline (IIIa)

In an autoclave, Pd on carbon at 10% by weight (0.022 g) is added to a solution of 0.51 grams of 6-fluoro-2,2,4-trimethyl-1,2-dihydroquinoline (IX) (2.67 mmol) in heptane (2 mL) and gaseous hydrogen is charged at a pressure of 3 bar. The mixture is heated to 30° C. for 2 hours, under vigorous stirring.

Subsequently, the catalyst is filtered off and the solvent is evaporated under reduced pressure obtaining 0.48 grams of 6-fluoro-2,2,4-trimethyl-1,2,3,4-tetradroquinoline (IIIa).

Example 4 (Comparative)

Preparation of (3R)-7-fluoro-1,1,3-trimethylindan-4-ylamine (I) by Means of Racemic Resolution of a Salt 1.7 g of racemic 7-fluoro-1,1,3-trimethylindan-4-ylamine (8.8 mmol) and 0.65 g of D-(2S,3S)-(−)-tartaric acid (4.4 mmol) are dissolved in methanol (4.0 mL). The mixture is then heated to 70° C. for one hour. Subsequently, it is cooled to room temperature with the formation of a white coloured precipitate. This heterogeneous mixture is cooled to 4° C. for 18 hours. The solid is filtered and recrystallized from methanol six times.

The salt thus obtained is mixed with an aqueous solution of sodium hydroxide at 10% by weight, until pH=12 is reached. Diethyl ether (20 mL) is added to the alkaline solution, the phases are separated and the aqueous phase is re-extracted with diethyl ether (20 mL). The combined organic phases are washed with water and dried over sodium sulphate.

The solvent is evaporated under reduced pressure obtaining 0.29 g of (3R)-7-fluoro-1,1,3-trimethylindan-4-ylamine (99.0% e.e.; yield=17.0%).

The invention claimed is:

1. A process for preparing a compound 1,1,3-trimethylindan-4-amine of formula (I), or a salt thereof, enriched in its (R) enantiomer:

(I)

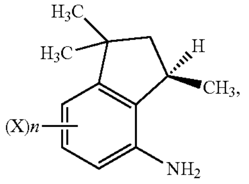

the process comprising:

treating a racemic mixture of an optionally substituted 2,2,4-trimethyl-1,2,3,4-tetrahydroquinoline compound of formula (IIIa)

(IIIa)

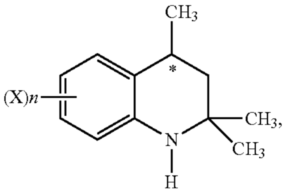

comprising an (R) enantiomer of formula (IVa) and an(S) enantiomer of formula (Va):

(IVa)

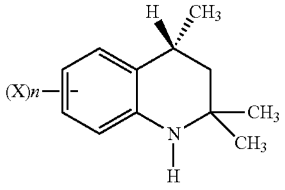

(Va)

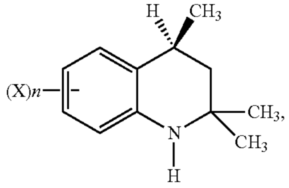

according to an operating sequence A, comprising:

(A1) converting by a protection reaction, the first racemic mixture of the compound of formula (IIIa) into a second racemic mixture of a compound of formula (IIIb) having a protecting PG group suitable to protect the nitrogen atom (IIIb)

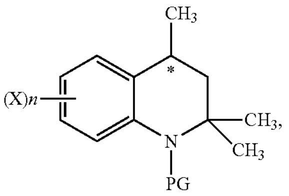

the racemic mixture of the compound of formula (IIIb) comprising an (R) enantiomer of formula (IVb) and an(S) enantiomer of formula (Vb)

(IVb)

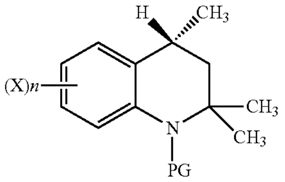

(Vb)

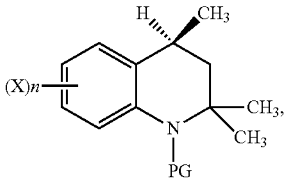

(A2) separating the (R) enantiomer of formula (IVb) from the(S) enantiomer of formula (Vb);

subjecting the (R) enantiomer of formula (IVb) obtained in the separating (A2) to an acid rearrangement to form a compound of formula (VI)

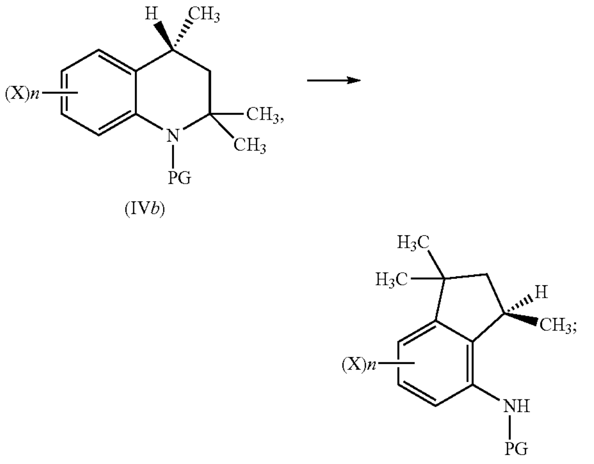

(IV*b*)

(VI)

substituting the PG group of the compound of formula (VI) with a hydrogen atom to obtain the (R) enantiomer of the compound of formula (I);

wherein, in the formulas,

* indicates an asymmetric carbon atom,

X is a fluorine atom, n is 1,

PG is a —$COR^1$ group or a —$COOR^2$ group, $R^1$ is methyl, $R^2$ is methyl or a benzyl group wherein, the optical purity of the compound of formula (VI) is greater than 97% ee.

2. The process of claim 1, further comprising, in sequence:

(i) oxidizing, with an oxidizing agent, an(S) enantiomer of formula (Vb) obtained in the separating (A2) to form a compound of formula (VII)

(VII)

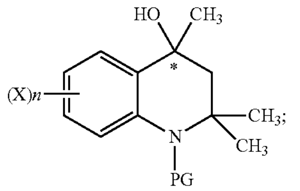

(ii) dehydrating the compound of formula (VII) in an acid environment to obtain a compound of formula (VIII)

(VIII)

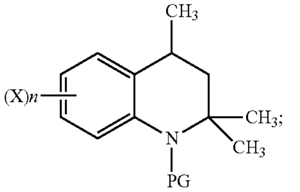

and (iii) hydrogenating the compound of formula (VIII) to obtain a racemic mixture of the compound of formula (IIIb) comprising the (R) enantiomer of formula (IVb) and the enantiomer of formula (Vb).

3. The process of claim 1, further comprising, in sequence:

(i) oxidizing, with an oxidizing agent, an(S) enantiomer of formula (Vb) obtained in the separating (A2) to form a compound of formula (VII)

(VII)

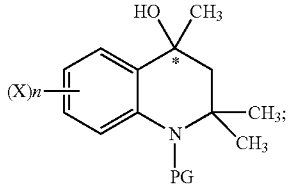

(ii) dehydrating the compound of formula (VII) in an acid environment to obtain a compound of formula (VIII)

(VIII)

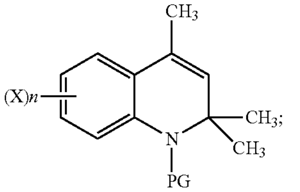

(ii-bis) converting, by a deprotection reaction the compound of formula (VIII) to obtain a compound of formula (IX)

(IX)

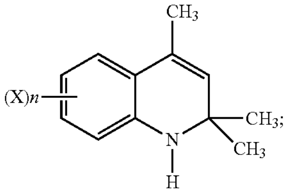

(iii-bis) hydrogenating the compound of formula (IX) to obtain a racemic mixture of the compound of formula (IIIa) comprising the (R) enantiomer of formula (IVa) and the(S) enantiomer of formula (Va).

4. The process of claim 2, wherein the racemic mixture of the compound of formula (IIIb) obtained in the hydrogenating (iii) is fed to the separating (A2).

5. The process of claim 3, wherein the racemic mixture of the compound of formula (IIIa) obtained in the hydrogenating (iii-bis) is fed to the treating of the racemic mixture of the optionally substituted 2,2,4-trimethyl-1,2,3,4-tetrahydroquinoline compound of formula (IIIa).

6. The process of claim 1, wherein the substituting of the PG group with a hydrogen atom is carried out by hydrolysis or catalytic hydrogenation.

7. The process of claim 1, wherein the separating (A2) is carried out by a chiral column chromatographic technique.

8. The process of claim 1, wherein the (R) enantiomer of formula (IVb) which is subjected to the acid rearrangement in the subjecting has an enantiomeric excess (ee %) with respect to the(S) enantiomer of formula (Vb) greater than 90%.

9. The process of claim 1, wherein the acid rearrangement reaction in the subjecting comprises reacting the (R) enantiomer of formula (IVb) in the presence of an inorganic acid comprising sulfuric acid and/or orthophosphoric acid.

10. The process of claim 1, wherein the compound of formula (I) obtained from the substituting of the PG group has an enantiomeric excess (ee %) of the (R) enantiomer with respect to the(S) enantiomer of greater than 97%.

11. The process of claim 8, wherein the enantiomeric excess is greater than 98%.

12. The process of claim 8, wherein the enantiomeric excess is greater than 99.5%.

13. The process of claim 1, wherein the compound of formula (I) is:

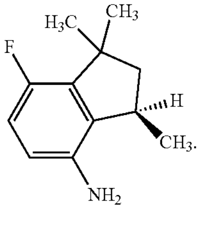

14. The process of claim 1, wherein the PG is acetyl group.

15. The process of claim 9, wherein the inorganic acid is added in an amount of between 3 and 10 molar equivalents with respect to the (R) enantiomer of formula (IVb).

16. The process of claim 9 wherein the acid rearrangement reaction is carried out at a temperature of from 10° C. to 60° C.

17. The process of claim 9 wherein the optical purity of the compound of formula (VI) is the same as the optical purity of (R) enantiomer of formula (IVb).

* * * * *